US008674033B2

(12) United States Patent
Hissink et al.

(10) Patent No.: US 8,674,033 B2
(45) Date of Patent: *Mar. 18, 2014

(54) BIODEGRADABLE PHASE SEPARATED SEGMENTED MULTI BLOCK CO-POLYMERS

(75) Inventors: Catharina Everdina Hissink, Groningen (NL); Ronald Meyboom, Haren (NL); Theodorus Adrianus Cornelius Flipsen, Groningen (NL)

(73) Assignee: Innocore Technologies B.V., Groningen (NL)

( * ) Notice: Subject to any disclaimer, the term of this patent is extended or adjusted under 35 U.S.C. 154(b) by 1411 days.

This patent is subject to a terminal disclaimer.

(21) Appl. No.: 10/521,126

(22) PCT Filed: Jul. 16, 2003

(86) PCT No.: PCT/NL03/00519
§ 371 (c)(1),
(2), (4) Date: Jul. 10, 2006

(87) PCT Pub. No.: WO2004/007588
PCT Pub. Date: Jan. 22, 2004

(65) Prior Publication Data
US 2007/0003592 A1    Jan. 4, 2007

(30) Foreign Application Priority Data
Jul. 16, 2002 (EP) ................... 02077878

(51) Int. Cl.
*C08G 18/00* (2006.01)
*A61K 31/74* (2006.01)
*C08G 63/08* (2006.01)

(52) U.S. Cl.
USPC .................. 525/440.01; 424/78.17; 525/450

(58) Field of Classification Search
None
See application file for complete search history.

(56) References Cited

U.S. PATENT DOCUMENTS

| 5,066,772 | A | * | 11/1991 | Tang et al. ............ 528/354 |
| 5,202,413 | A |   | 4/1993  | Spinu |
| 6,160,084 | A |   | 12/2000 | Langer et al. |
| 2001/0009662 | A1 | * | 7/2001 | Cohn et al. ............ 424/78.17 |

OTHER PUBLICATIONS

Penco et al. "New Poly(ester-carbonate) Multi-block Copolymers Based on Poly(lactic-glycolic acid) and Poly(ε-caprolactone) Segments"; Macromolecular Chemistry and Physics 199, pp. 1737-1745 (1998).*
Penco et al. "New Poly(ester-carbonate) Multi-block Copolymers Based on Poly(lactic-glycolic acid) and Poly(E-caprolactone) Segments"; Macromolecular Chemistry and Physics 199, pp. 1737-1745 (1998).*
Penco, et al. "New poly(ester-carbonate) multi-block copolymers based on poly(lactic-glycolic acid) and poly(ε-caprolactone) segments," *Macromol. Chem. Phys*, vol. 199, pp. 1737-1745 (1998).

* cited by examiner

*Primary Examiner* — Robert A Wax
*Assistant Examiner* — Jeffrey T Palenik
(74) *Attorney, Agent, or Firm* — Hoffmann & Baron LLP

(57) ABSTRACT

The invention is directed to biodegradable, thermoplastic, phase separated segmented multi-block copolymers. The copolymers of the present invention find use in various biomedical applications as well as in pharmaceutical applications. According to the invention, a biodegradable, phase separated copolymer is provided, comprising segments of a soft prepolymer (A) having a glass transition temperature, Tg, lower than 37° C.; and segments of a hard prepolymer (B) having a phase transition temperature, Tm, of 40-100° C.

24 Claims, 6 Drawing Sheets

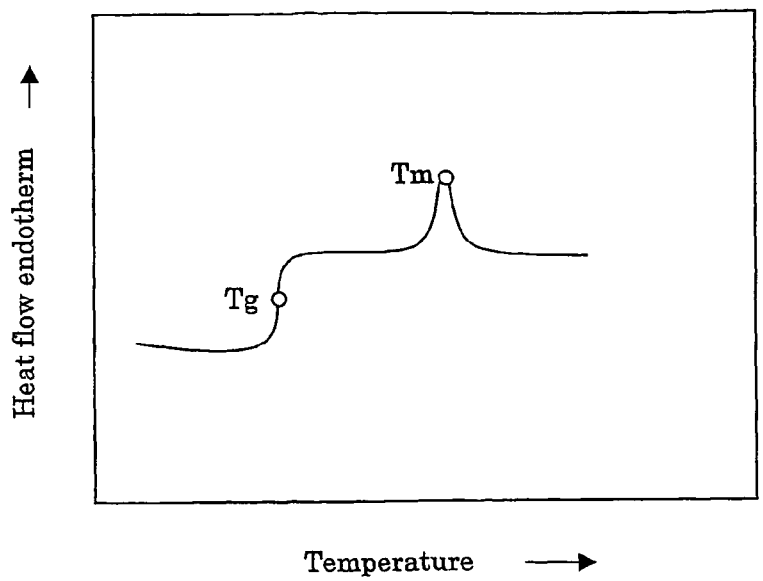
Figure 1: phase separation in a polymer

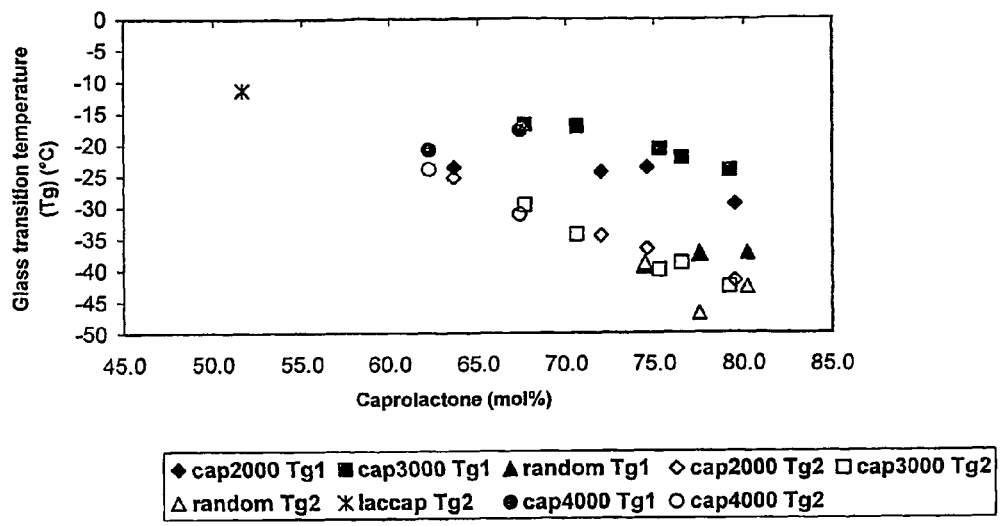
Figure 2: Glass transition temperature vs caprolactone content
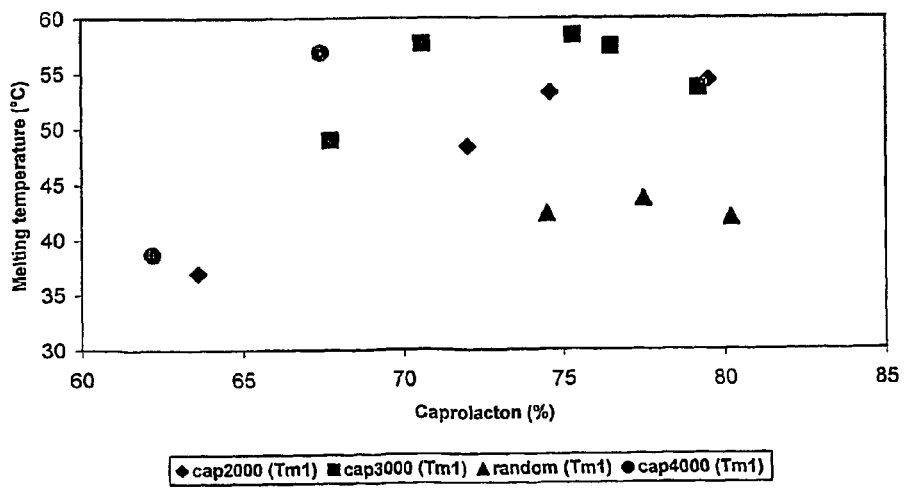
Figure 3: Melting temperature vs caprolactone content

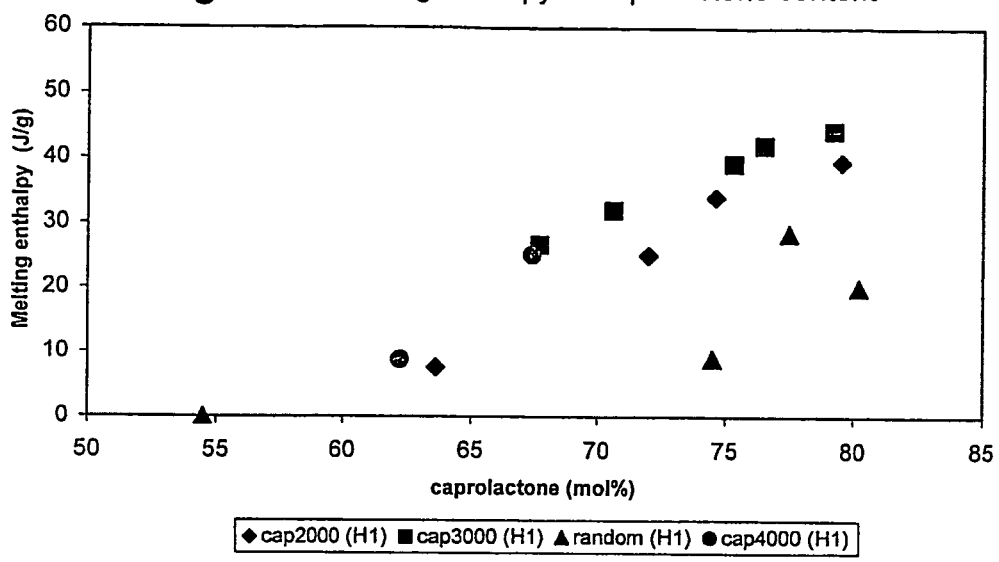
Figure 4: Melting enthalpy vs caprolactone content

Figure 5: Melting enthalpy vs average caprolactone sequence length
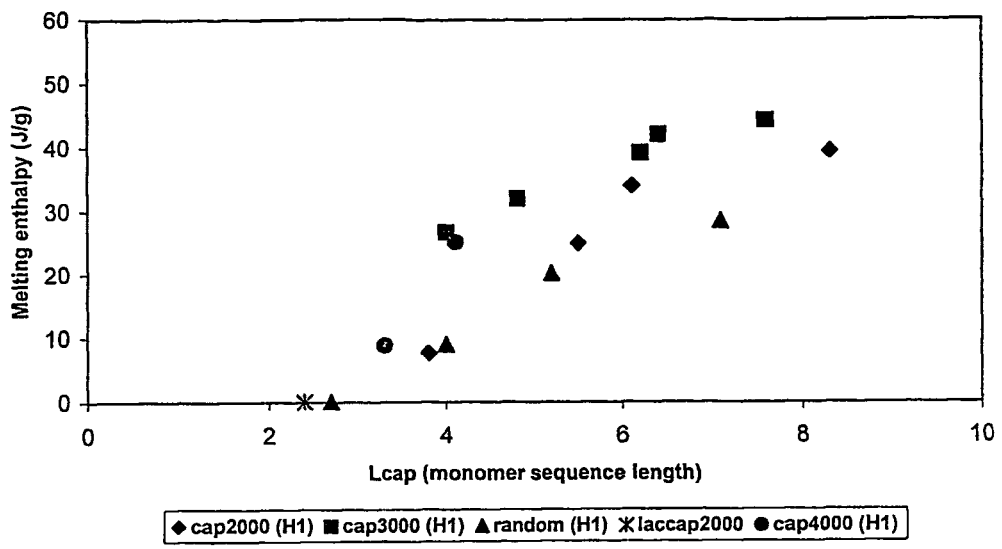
Figure 6: Average caprolactone sequence length vs caprolactone content
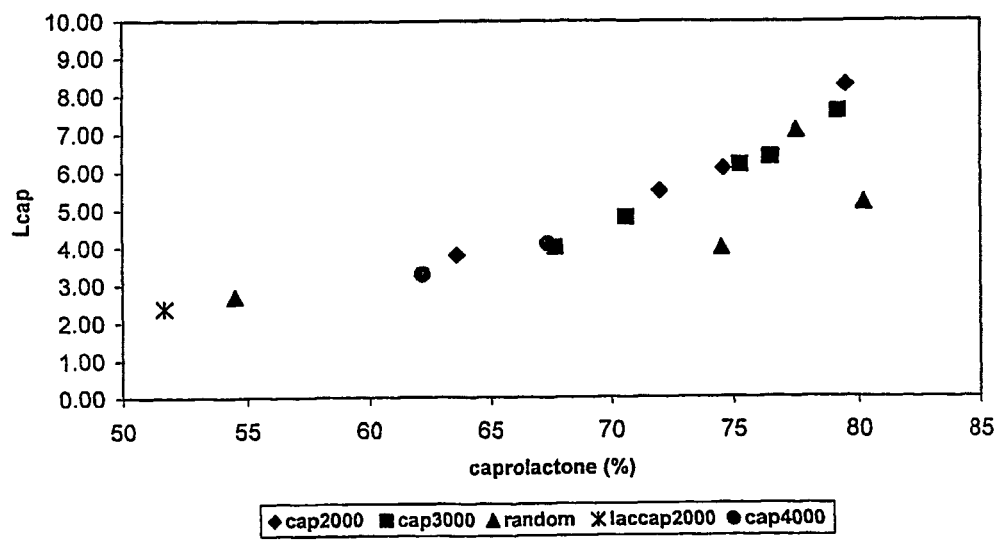

Figure 7: Stress vs strain of copolyesters with cap3000 pre-polymer
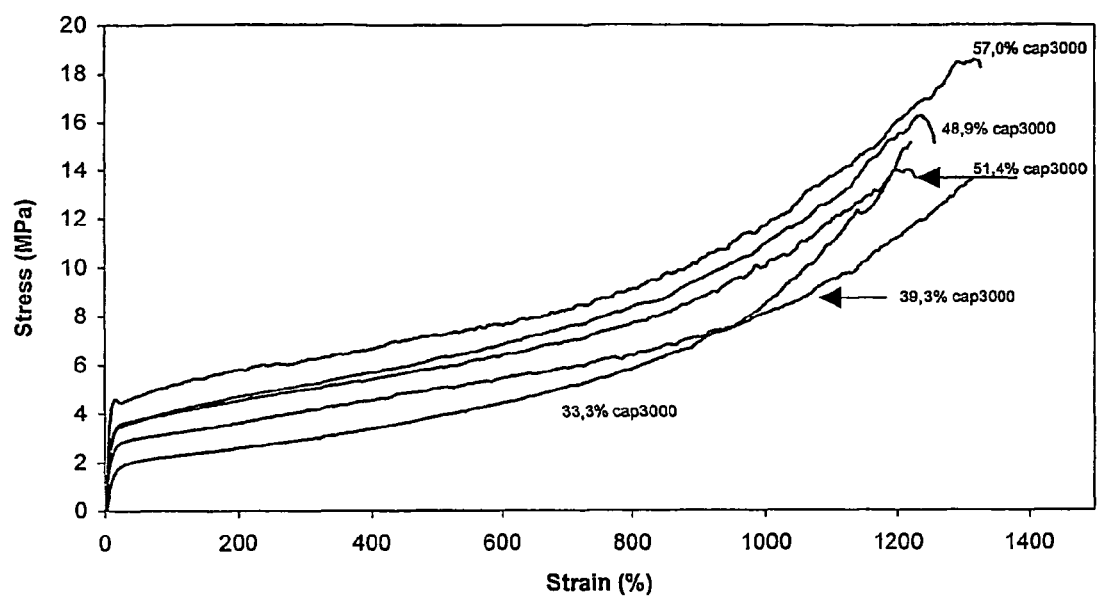

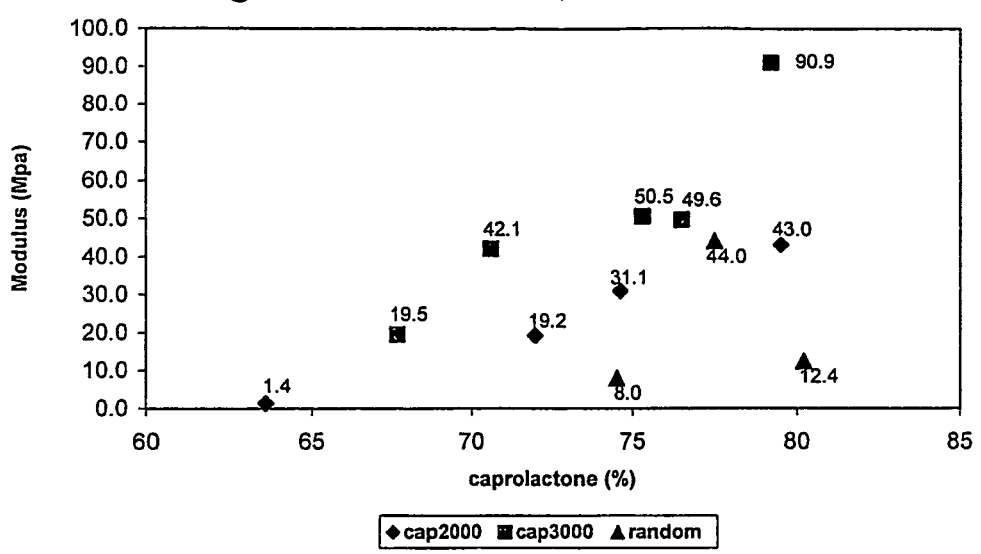

BIODEGRADABLE PHASE SEPARATED SEGMENTED MULTI BLOCK CO-POLYMERS

This application is the U.S. National Phase of International Application Number PCT/NL2003/000519 filed on 16 Jul. 2003, which is incorporated herein by reference.

BACKGROUND OF TILE INVENTION

The invention is directed to biodegradable, thermoplastic, phase separated segmented multiblock copolymers. The copolymers of the present invention find use in various biomedical as well as pharmaceutical applications.

Generally, thermoplastic phase separated co-polymers consist of a low glass transition temperature (Tg), flexible 'soft', amorphous, segment and a high Tm (semi)crystalline 'hard' segment which are incompatible or only partially compatible.

Examples of phase separated segmented/block copolymers are found e.g. in U.S. Pat. No. 6,255,408, U.S. Pat. No. 5,554,170, U.S. Pat. No. 5,066,772, U.S. Pat. No. 5,236,444, U.S. Pat. No. 5,133,739 and U.S. Pat. No. 4,429,080. These known materials are bioresorbable co-polyesters wherein the hard blocks are predominantly build of crystalline poly-glycolide and/or poly-lactide. Glycolide rich polyesters are especially suitable for fast resorbable biomedical articles such as mono- or multi filament sutures; lactide rich polyesters are used in more slowly resorbing medical applications, such as nerve guides, nerve graft and many other products. However, the high melting point of the poly-glycolide or poly-L-lactide rich blocks requires very high polymerisation and processing temperatures (about 200° C.), which may result in unwanted degradation behavior and/or trans-esterification. Furthermore, the poly-glycolide rich polyesters are unsuitable for applications for which a slow resorption is needed.

As an alternative to polyglycolide rich polyesters, poly-L-lactide rich copolyesters have been suggested as materials which have a higher resorption time and very good mechanical properties as a result of the crystalline segments. However, the use of a semi-crystalline random copolymer of L-lactide and ε-caprolactone (50/50) for bridging of peripheral nerve defects and of highly crystalline poly-L-lactide as bone plates have caused some severe problems in the past. Mild to severe foreign body reactions were observed after 2 to 3 years of implantation, respectively, due to the presence of long-lasting biomaterial fragments. (Den Dunnen et al. (Microsurgery 14 (1993) 508-515); Rozema et. al. In: P. J. Doherty, R. L. Williams, D. F. Williams, eds. "Biomaterial-Tissue interfaces. Advances in biomaterials" 10 Amsterdam, Elsevier Science Publishers B. V. (1992) 349-355). It is an object of the present invention to provide a new biodegradable, thermoplastic, phase separated segmented multi-block copolymer, which does not suffer from the above-mentioned disadvantages and thus opens possibilities for new medical applications.

SUMMARY OF THE INVENTION

The copolymer of the invention is composed of at least two different segments each having different physical characteristics, including degradation characteristics, and is characterized by good mechanical properties, in particular good tensile strength, elongation and elastic properties. Due to their phase separated morphology, the materials of the present invention should also be suitable for constructing drug delivery matrices and drug eluting coatings, which may be used to enclose a certain therapeutic agent and to release the this agent at a desired time and/or location.

It has been found that these properties can be obtained by a biodegradable, phase separated copolymer, comprising segments of a soft biodegradable prepolymer (A) having a Tg not more than 37° C.; and segments of a hard biodegradable prepolymer (B) having a phase transition temperature of 40-100° C., in which copolymer the segments are linked by a multifunctional chain-extender.

The term "phase-separated", as used herein, refers to a system, in particular a copolymer, build of two or more different prepolymers, of which at least two are incompatible with each other at temperatures of 40° C. or below (when kept at body conditions). Thus the prepolymers do not form a homogeneous mixture when combined, neither when combined as a physical mixture of the prepolymers, nor when the prepolymers are combined in a single chemical species as "chemical mixture", viz. as copolymer.

The term "prepolymer" refers to the chemical units or building blocks making up the copolymer of the present invention. Each prepolymer may be obtained by polymerization of suitable monomers, which monomers thus are the building blocks of each prepolymer. The desired properties of the prepolymers and, by consequence, of the copolymer of the present invention, may be controlled by choosing a prepolymer of a suitable composition and molecular weight (in particular Mn), such that the required Tm or Tg is obtained.

The morphology of the polymer (or of the device made thereof) is dependent on the environmental conditions: a DSC measurement may be performed under inert (dry) conditions and the results may be used to determine the dry materials' thermal properties. However, the morphology and properties at physiological conditions (i.e., in the body) and ambient conditions (room temperature) may be different. It is to be understood that the transition temperatures, Tg and Tm as used herein, refer to the corresponding values of a material when applied in vivo; viz. when at equilibrium with an atmosphere that is saturated with water vapor and at body temperature. This may be simulated in vitro by performing the DSC measurement after allowing the material to equilibrate with a water-saturated atmosphere (typically this may take several minutes to one hour). When in dry state, the materials used in the present invention may have Tg values that are somewhat higher than at mammalian body conditions, that is to say, when the dry materials are subjected to DSC, the first inflection point may arise at higher temperatures, for instance at 42 or 50° C., or more. Upon application in vivo, however, the dry material's Tg and/or Tm will drop as a result of the absorption of water and this final Tg should be about body temperature or lower according to the present invention. The final Tm should be present at temperatures between 40-100° C.

For instance, a polymer that contains PEG in the soft segment can be crystalline under dry conditions at ambient temperature, while amorphous under wet conditions, giving a mixed Tg or two separated Tg's of the soft segment formed by amorphous softened PEG and the polyester/carbonate. The phase-separated quality of the copolymers of the present invention is reflected in the profile of the glass transition temperature (Tg) or melting temperature (Tm). Whereas a single prepolymer is usually characterized by a single phase transition (Tg or Tm), the phase-separated copolymers are characterized by at least two phase transitions, each of which is related to (but not necessarily identical to) the corresponding Tg or Tm values of the prepolymers which are comprised in the copolymer. Prepolymers which would form an (ideal) mixture or blend would result in a copolymer having a single Tg or Tm. The glass transition temperature, Tg, is determined by tailing the midpoint of the specific heatjump, as may be measured e.g. by differential scanning calorimetry (DSC). The melting temperature, Tm, is the peak maximum of the melting peak, as is schematically illustrated in FIG. 1, that shows the heat flow endotherm for a copolymer characterized by a Tg and a Tm. As defined herein, values of Tg and Tm of a certain prepolymer reflect the values as measured on the copolymer. For instance, the Tg of the soft segment is the Tg measured on the copolymer. In case of complete immiscibility of the prepolymers, the Tg of the copolymer is governed solely by the Tg of the amorphous, "soft" prepolymer. In most cases, however, the composition of the hard and the soft segments of the copolymer is not exactly the same as the composition of the prepolymers from which the copolymer is prepared. Part of the original hard segment forming prepolymer will mix with the soft prepolymer and thus become part of the soft phase. The Tg value of the soft segment is then different from that of the prepolymer used. The extent of miscibility (and therefore the deviation of Tg and/or Tm from those of the corresponding pre-polymers) is dependent on the prepolymer composition, ratio and -segment length in the copolymer. In case a semi-crystalline prepolymer is used for building the hard segment, the amorphous part of this segment may also be immiscible with the other amorphous prepolymer segment, thus resulting in two different glass transition temperatures, both being more or less similar to the glass transition temperatures of their respective prepolymers. In case the soft segment is semi-crystalline (e.g. when polyethyleneglycol, PEG, is part of the pre-polymer), the polymer may consist of two crystalline phases: one as part of the soft segment and one in the hard segment. The low and high temperature phase transitions that characterize the phase separated copolymers of this invention are predominantly determined, by the contributions of the respective soft- and hard segments forming the biodegradable pre-polymers. On the one hand Tg and Tm of the final copolymer may be entirely determined by the corresponding values of the pre-polymers. On the other hand deviations from these "ideal" values may occur, as a result of partly phase mixing, which in practice is frequently observed.

The Tg of the copolymer segments generally lies between the value of the phase mixed copolymer and those of the separate prepolymers.

The multi-block copolymers of this invention have advantages over the block-copolymers known from the prior art, e.g. the block copolymers of structure ABA as mentioned in the examples of the introduction. Although polymer properties can be greatly improved by using block copolymers with blocks of different copolymers instead of homo- or random copolymers, they still have some disadvantages.

To obtain a minimum molecular weight of the copolymer, the sequences A and B must have a certain length. The blocks may independently behave as the individual homopolymers with similar composition. Properties of the ABA type copolymers can only be tuned by varying the composition of A and B blocks. Another disadvantage is that blockcopolymers must be prepared at relatively high temperatures (>100° C.) under inert conditions for complete conversion of all the monomers and to obtain sufficient molecular weight. The first disadvantage can be solved by using multiblock copolymers wherein the blocks or segments are much shorter and linked together by a chemical reaction. Properties such as degradation behaviour can be tuned in a much better way by choosing the proper combination of segment lengths, ratio and composition.

Furthermore, by the process of preparing ABA block copolymers (and derivatives thereof), there is always a possibility of transesterification, resulting in a certain extent of phase mixing.

The multiblock copolymers of the present invention do not suffer from this disadvantage since they can be prepared by linking pre-polymers with previously determined monomer composition at rather low temperatures (<100° C.) thus avoiding trans-esterification and other side-reactions reactions, which may cause the generation of undesired degradation and other by-products. This means that the monomer sequence length of the copolymer is determined by the choice of building components and not so much by reaction time and temperature, as being usually applied for synthesis of random copolymers. An advantage of multi-block copolymers of this invention prepared by linking of pre-polymers using a multi-functional chain-extender is that pre-polymer segments may be randomly distributed in the copolymer by choosing all possible prepolymer ratios and segment lengths, thus offering much more possibilities of tuning the properties.

Known multiblock copolymers of two types of biodegradable prepolymers on the other hand, can only be made in an alternating pre-polymer sequence, resulting in a limited range of possible variables. (M. Penco, F. Bignotti, L. Sartore, S. D'Antone and A. D'Amore, J. Appl. Pol. Sci. Vol. 78, 1721-1728 (2000).

Another advantage of the copolymers of the present invention is that they may be based on multifunctional (aliphatic) chain-extenders. By choosing the type and amount of chain-extender the polymers properties can be effected (for instance, the chain-extender may act as a softener or it may effect the degree of phase separation). The total degree of freedom to obtain polymers with the desired properties is therefore increased compared to polymers of the prior art.

Biodegradable phase separated polyesters or polyester-carbonates of this invention are a promising group of biomaterials and can be used in various biomedical applications since they exhibit good mechanical, elastic and processing properties. Furthermore, they can be used in pharmaceutical applications, e.g. for drug delivery.

Biodegradable multi-block copolymers containing one hydrolysable polyester segment and one hydrophilic hydrolytically stable segment have been studied for their drug loading and release capacity e.g. poly(caprolactone)-polyethyleneglycol (PEG) multiblock copolymers are described by Lee et. al., J. Control. Release. 73 (2001) 315-27. The multiblock copolymers of the present invention are different from these known copolymers by the presence of at least two biodegradable segments instead of only one, therefore offering more possibilities of varying the degradation and drug release properties.

The mechanical and degradation properties of the multi block copolymers can be easily tuned by changing the type of monomers of the soft and hard segment forming pre-polymers and their chain length and -ratio and by choosing the type and amount of chain-extender. Furthermore, the thermal properties are low enough for processing the polymer in the melt and high enough to be used as a biomedical device. The monomer ratio and -distribution of the copolymer can be easily controlled by varying the polymerization conditions.

A crystalline hard segment is usually desired to obtain elastomeric and tough, non-sticky materials. A low Tg of the soft segment is usually necessary to obtain high elasticity. The phase separated character of the copolymers of the invention is very important for applications where good mechanical properties are required (such as porous scaffolds), since it enables that the hard segments may contribute to the mechanical strength, whereas the soft segments provide for the desired elastic properties. For drug delivery purposes, mechanical properties are less important, but the difference in physical properties of the two phases are essential. As mentioned previously, a prerequisite of the biomedical phase separated segmented co-polyester is that the melting point (i.e., phase transition temperature) of the polyester hard segment is larger than 40° C.: the phase separated morphology must also be present at body temperature and environment in order to retain the initial mechanical properties and structure of the device after implantation. An important class of segmented co-polyesters with such a good phase separation are those based on crystalline poly-ε-caprolactone hard segments. For example, a different approach to obtain semi-crystallinity in a lactide-ε-caprolactone copolymer not derived from long L-lactide sequences as in the previously mentioned L-lactide-ε-caprolactone copolymer, is the use of a phase separated copolymer of dl-lactide and ε-caprolactone with a monomer ratio that results in crystallization of the caprolactone part of the copolymer. Since the rate of degradation of poly-ε-caprolactone is low, especially in the crystalline phase, it is also a good way to lower the degradation rate of the copolymer. In this way, biocompatible biomedical articles of ε-caprolactone rich copolymers can be applied in situations when a slow resorbing rate is desired without the use of a major L-lactide content. The low melting temperature of the crystalline phase (50-60° C.) makes this copolymer very easy to process.

This crystalline phase will have a melting point that is similar to or only a little lower than that of the high molecular weight homopolymer of ε-caprolactone (60-65° C.). To obtain a thermoplastic elastomer with a modulus that is not too high, the content of this hard phase can be rather low (either dispersed or in a co-continuous system with the rubber phase).

Generally, the desired phase separated morphology (reflected by one melting point and at least one low Tg value) may be obtained by varying the composition, e.g. by choosing the number average molecular weight, Mn, of the A and B prepolymers. It is also possible to influence the phase separated morphology by varying the A/B ratio.

Although random copolymers of lactide and ε-caprolactone with a crystallisable ε-caprolactone content have been prepared in the past, the phase separation is not as good as in the phase separated segmented/block co-polymers of this invention. This is proven by the much lower melting temperature of the crystalline s-caprolactone segment, lower melting enthalpies (ΔH) and lower values of Tg (more amorphous ε-caprolactone present in the soft phase) of the random copolymers (see e.g. Hiljainen-Vainio et al., Lemmouchi et al., US-A-4 643 734).

DETAILED DESCRIPTION OF THE INVENTION

General Polymer Structures

The segmented multiblock copolymers of this invention consist of a soft segment which is preferably completely amorphous at body conditions, hydrolysable and with at least one phase transition being a Tg below 37° C. or preferably below 25° C. (as measured at body conditions). This segment will also be referred to herein as phase A. The copolymers of the present invention also contain a hard segment, consisting of a biodegradable crystalline or semi-crystalline polymer with a phase transition larger than 40° C. but smaller than 100° C. (as measured at body conditions) (phase B). The prepolymers A and B that form the "soft" and "hard" segments are linked by a multifunctional chain-extender. The "hard" and "soft" phases are incompatible or only partially compatible at body conditions. The multifunctional chain-extender is preferably an aliphatic molecule.

The resulting multiblock copolymers of the present invention preferably have a structure according to any of the formulae (1)-(3):

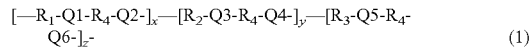

$$[-R_1-Q1-R_4-Q2-]_x-[R_2-Q3-R_4-Q4-]_y-[R_3-Q5-R_4-Q6-]_z- \quad (1)$$

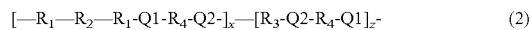

$$[-R_1-R_2-R_1-Q1-R_4-Q2-]_x-[R_3-Q2-R_4-Q1]_z- \quad (2)$$

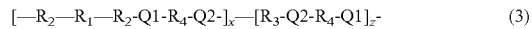

$$[-R_2-R_1-R_2-Q1-R_4-Q2-]_x-[R_3-Q2-R_4-Q1]_z- \quad (3)$$

wherein $R_1$ is part of phase (A) and may be amorphous polyester, amorphous polyetherester or amorphous polycarbonate; or an amorphous prepolymer that is obtained from combined ester, ether and/or carbonate groups. $R_1$ may contain polyether groups, which may result from the use of these compounds as an polymerization initiator, the polyether being amorphous or crystalline at room temperature. However, the polyether thus introduced in $R_1$ will become amorphous at physiological conditions and therefore belongs to phase (A).

The initiator is generally a multifunctional molecule, which initiates the (ringopening) polymerization. Suitable initiators are butanediol, PEG and diacids.

$R_2$ mainly or entirely contributes to phase (B) and may be a crystalline or semi-crystalline polyester, polyetherester, polycarbonate or polyanhydride; or pre-polymers of combined ester, ether, anhydride and/or carbonate groups. It is possible that part of phase $R_2$ is amorphous, in which case this part of R2 will contribute to phase (A).

$R_1$ and $R_2$ are not the same.

z is zero or a positive integer.

$R_3$ is a polyether, such as poly(ethylene glycol), and may be present (z≠0) or not (z=0). $R_3$ will be part of the soft phase A under physiological conditions.

$R_4$ is an aliphatic $C_2$-$C_8$-alkylene group, optionally substituted by a $C_1$-$C_{10}$ alkylene, the aliphatic group being linear or cyclic. $R_4$ is preferably a butylene, —$(CH_2)_4$—, group. The $C_1$-$C_{10}$ alkylene side group may contain protected S,N,P or O moieties. x and y are both a positive integer.

Q1-Q6 are linking units obtained by the reaction of the prepolymers with the multifunctional chain-extender. Q1-Q6 may be independently selected from amine, urethane, amide, carbonate, ester and anhydride. The event that all linking groups Q are different being rare and is usually not preferred.

Typically, one type of chain-extender may be used with three pre-polymers having the same end-groups resulting in a copolymer of formula (1) with six similar linking groups.

In case pre-polymers $R_1$ and R2 are differently terminated, two types of groups Q will be present: e.g. Q1 and Q2 will be the same between two linked segments $R_1$, but Q1 and Q2 are different when $R_1$ and R2 are linked. In copolymers of formula (2) and (3) the groups Q1 and Q2 are the same when two pre-polymers are present both terminated with the same end-group (which is usually hydroxyl) but are different when the pre-polymers are differently terminated (e.g. PEG which is diol terminated and a di-acid terminated 'tri-block' pre-polymer). The examples of formula (1), (2) and (3) show the result of the reaction with a difunctional chain-extender and difunctional prepolymers.

With reference to formula (1) the polyesters of the present invention may also be represented as multi-block or segmented copolymers having a structure (ab)n or a random distribution of segments (ab)r, wherein 'a' corresponds to the segment $R_1$ that forms phase (A) and 'b' corresponds to the segment $R_2$ that forms phase (B) (for z=0). In (ab)r, the a/b ratio (corresponding to x/y in formula (1)) may be unity or away from unity. The pre-polymers can be mixed in any desired amount and can be coupled by a multifunctional chain extender, viz. a compound having at least two functional groups by which it can be used to chemically link the pre-polymers. Preferably this is a difunctional chain-extender. In case z≠0, then the presentation of a random distribution of all the segments can be given by (abc)r were three different pre-polymers (one being a polyethyleneglycol) are randomly distributed in all possible ratio's. The alternating distribution is given by (abc)n. Alternating means in this case that two equally terminated pre-polymers (either a and c or b and c) are alternated with a differently terminated prepolymer b or a, respectively, in an equivalent amount (a+c=b or b+c=a). Those according to formula (2) or (3) have a structure (aba)n and (bab)n wherein the aba and bab 'triblock' pre-polymers are chain-extended with a di-functional molecule. In case the triblock prepolymer has the (aba)n structure, the 'a' segment should be essentially free of PEG, because the coupling reaction by ringopening can otherwise not be carried out successfully.

The method to obtain a copolymer with a random distribution of a and b (and optionally c) is far more advantageous than when the segments are alternating in the copolymer such as in (ab)n with the ratio of prepolymers a and b being 1. The composition of the copolymer can then only be determined by adjusting the pre-polymer lengths. In general, the a and b segment lengths in (ab)n alternating copolymers are smaller than blocks in block-copolymers with structures ABA or AB.

The pre-polymers of which the a and b (and optionally c) segments are formed in (ab)r, (abc)r, (ab)n and (abc)n are linked by the difunctional chain-extender. This chain-extender is preferably a diisocyanate chain extender, but can also be a diacid or diol compound. In case the pre-polymers all contain hydroxyl end-groups, the linking units will be urethane groups. In case (one of) the prepolymers are carboxylic acid terminated, the linking units are amide groups. Multi-block copolymers with structure (ab)r and (abc)r can also be prepared by reaction of di-carboxylic acid terminated pre-polymers with a diol chain extender or vice versa (diol terminated pre-polymer with diacid chain-extender) using a coupling agent such as DCC (dicyclohexyl carbodimide) forming ester linkages. In (aba)n and (bab)n the aba and bab prepolymers can also be linked by a difunctional chain-extender The term "Randomly segmented" copolymers refer to copolymers that have a random distribution (i.e. not alternating) of the segments a and b: (ab)r or a, b and c: (abc)r.

Polymerisation Method and Conditions:

Segmented multiblock co-polymers with structure (ab)r and (abc)r can be made by chain-extending a mixture of the pre-polymers, containing the hard- and the soft segment forming monomers of segments $R_1$ and $R_2$, and optionally $R_3$, in the desired ratio with an equivalent amount of a di-functional molecule, preferably an aliphatic molecule, more preferably a diisocyanate such as 1,4-butanediisocyanate (BDI). Preferably, the reaction is carried out in the bulk at a temperature at which the pre-polymer mixture is a melt and which is at least 20° C. higher than the highest phase transition temperature of one of the pre-polymers.

Polymerization takes place for a time long enough to obtain an intrinsic viscosity of the copolymer of preferably 1 dl/g or higher. Solid state post polymerisation at room temperature may increase the molecular weight to an intrinsic viscosity up to 4 dl/g. The specific polymerisation time and temperatures for this bulk polymerisation are given in some examples below, but may be different for other pre-polymer combinations. This bulk polymerisation method is also applicable to segmented co-polymers with structures (aba)n and (bab)n. The low polymerisation temperature and short polymerisation time will prevent from trans-esterification so that the phase separated morphology is obtained and the monomer distribution is the same as in the pre-polymers that build the copolymer. On the contrary, high molecular weight random copolymers have to be prepared at higher temperatures (>100° C.) and for a much longer time to obtain a full incorporation of all the monomers. During that time trans-esterification reactions will occur and a more random (which is less blocky) monomer distribution is obtained.

The alternating multi block-copolymers (ab)n are preferably formed by reacting (end-capping) one of the pre-polymers with at least two equivalents of a di-functional chain-extender, preferably diisocyanate, in the bulk, removing the excess of chain-extender and than add the other pre-polymer in about 1:1 ratio. In case of copolymers with structure (abc)n, two pre-polymers can simultaneously be end-capped in the desired ratio and subsequently chain-extended with an equivalent amount of the $3^{rd}$ prepolymer, or vice versa: one pre-polymer can be end-capped and then chain extended with an equivalent amount of a mixture of two prepolymers. The polymer can be made either in bulk or in solution, although the chain-extend reaction is preferred to be carried out in solution.

The materials obtained by chain-extending in the bulk can also be produced in situ in an extruder.

The segmented copolymers of structures (ab)r, (abc)r or (aba)n or (bab)n can also be made in solution. The pre-polymer(s) are dissolved in an inert organic solvent and the chain-extender is added pure or in solution. The polymerisation temperature can be the same or even lower than the highest phase transition temperature of the pre-polymers. Coupling reactions with DCC are preferably carried out in solution. Two (or three) prepolymers that are all diol or diacid terminated are mixed in solution with a diacid or diol terminated chain-extender, respectively, after which DCC is added.

Pre-polymers of which the multi-block copolymers with structures (aba)n or (bab)n can be prepared, are generally made by addition of the monomer(s) of which the outer block will be formed to a pre-polymer with monomers that form the inner block. These methods are known in the art. Since the aba and bab pre-polymers are build of relatively short segments, the pre-polymer is subsequently chain-extended with a di-functional molecule by the method described above.

If the chain-extender is a difunctional, aliphatic molecule and the pre-polymers are linear, a linear co-polymer is made; if one of the reactants (either the chain-extender or at least one of the pre-polymers) or both have more than two functional groups, cross-linked structures are obtained. Preferably, the chain-extender is an aliphatic di-isocyanate such as 1,4-butanediisocyanate.

The combination of hard- and soft phase forming pre-polymers or monomers is chosen in such a way to obtain a phase separated segmented or block co-polyester or polyester-carbonate with the desirable degradation, mechanical, physical and thermal properties. Since the two phases are chemically linked, the border of the phases is partly mixed and will result in good mechanical properties of the copolymer, even when the hard and soft segment are completely incompatible.

Pre-polymers: Composition and Method of Preparation

The hydrolysable segment $R_1$ of formula (1) forming the soft phase A is obtained by reaction of pre-polymer A.

Pre-polymer (A) may e.g. be prepared by ring-opening polymerisation. Thus a prepolymer (A) may be a hydrolysable co-polymer prepared by ring-opening polymerisation initiated by a diol or di-acid compound, preferably having a random monomer distribution. The diol compound is preferably an aliphatic diol or a low molecular weight polyether such as polyethyleneglycol (PEG). The polyether can be part of the pre-polymer (A) by using it as an initiator or it can be mixed with the pre-polymer A, thus forming hydrophilic segment $R_3$ in formula (1). Pre-polymer (A) may be a hydrolysable polyester, polyetherester, polycarbonate, polyestercarbonate, polyanhydride or copolymers thereof, derived from cyclic monomers such as lactide (L,D or L/D), glycolide, ε-caprolactone, δ-valerolactone, trimethylene carbonate, tetramethylene carbonate, 1,5-dioxepane-2-one, 1,4-dioxane-2-one (para-dioxanone) or cyclic anhydrides (oxepane-2,7-dione). To fulfill the requirement of a Tg below 37° C. of the soft segment, some of the above-mentioned monomers or combinations of monomers are more preferred than others. For example, pre-polymers (A) containing the monomers lactide and/or glycolide are preferably combined with any of the other mentioned cyclic co-monomers (ε-caprolactone, δ-valerolactone, trimethylenecarbonate, 1,4 dioxane-2-one and combinations thereof). This may by itself lower the Tg, or the pre-polymer is initiated with a polyethylene glycol with sufficient molecular weight to lower the glass transition temperature of the soft segment.

Furthermore, pre-polymer A can be based on (mixtures of) condensation type of monomers such as hydroxyacids (e.g. lactic acid, glycolic acid, hydroxybutyric acid), diacids (e.g. glutaric, adipic or succinic acid, sebacic acid) and diols such as ethyleneglycol, diethyleneglycol, 1,4-butanediol or 1,6-hexanediol forming ester and/or anhydride hydrolysable moieties.

The segment $R_2$ of formula (1), forming the hard phase (B) may be obtained by reaction of prepolymers (B) containing any hydrolysable, biocompatible polyester, polyetherester, polyestercarbonate, polyanhydride or copolymers thereof, and derived from both cyclic and non-cyclic monomers that are also used for building the pre-polymer (A), having a phase transition between 40° C. and 100° C. Examples of the hard phase forming pre-polymers are poly(ether)esters containing a crystallisable amount of ε-caprolactone, δ-valerolactone or para-dioxanone, polyhydroxyalkanoates, aliphatic polyanhydrides. Polymers of formula's (2) and (3) are composed of segments R1 and R2 with monomer compositions similar to those of formula (1), except for R1 of formula (2) that can not comprise a polyethyleneglycol initiator. Pre-polymers containing aromatic groups are generally not suitable for the hard phase forming pre-polymer, because they have a transition temperature that is too high (>100° C.). Furthermore, the processing temperature is high, the solubility in common organic solvents is generally too low and pre-polymers containing aromatic groups may give rise to undesired degradation products. This also holds for the chain-extenders used; although chain-extenders containing aromatic groups can be used, this is generally not preferred because of the undesired degradation products and the transition temperature that is too high. Therefore, aliphatic chain extenders are preferred.

Typically pre-polymer (B) has a Mn of larger than 1000, preferably larger than 2000, more preferably larger than 3000, which numbers particularly hold for the case where prepolymer (B) is poly-ε-caprolactone. In general Mn of prepolymer (B) will be less than 10000. The content of prepolymer (3) in the copolymer is preferably 10-90 wt.%, more preferably 25-70 wt %, most preferably 30-50 wt.% (particularly for poly-ε-caprolactone).

The L/D ratio of the lactide used in amorphous poly-dl-lactide blocks or segments may be away from unity (other than 50/50). For instance, an L/D ratio between 85/15 and 15/85 gives an completely amorphous homo-polymer. Furthermore, it is known that an excess of one isomer (L or D)over the other increases the Tg of the poly-dl-lactide. A minor amount of any other of the above mentioned monomers that build the soft phase may also be present in the hard phase forming pre-polymer or block.

The pre-polymers will preferably be linear and random (co)polyesters, polyester-carbonates, polyetheresters, or polyanhydrides with reactive end-groups. These end-groups may be hydroxyl or carboxyl. It is preferred to have a dihydroxy terminated co-polymer, but hydroxy-carboxyl or dicarboxyl terminated polymers can also be used. In case the polymer has to be linear, it can be prepared with a di-functional component (diol) as a starter, but in case a three or higher functional polyol is used star shaped polyesters may be obtained. The diol can be an aliphatic diol or a low molecular weight polyether.

The pre-polymer synthesis by a ring opening polymerisation is preferably carried out in the presence of a catalyst. A suitable catalyst is $Sn(Oct)_2$ with M/I=5000-30000. It is also possible to carry out the synthesis without a catalyst.

The conditions for preparing the polyesters, polycarbonates and polyanhydrides are those known in the art.

The copolymers of the present invention are generally linear. However, it is also possible to prepare the copolymers in a branched or cross-linked form. These non-linear copolymers of the present invention may be obtained by using a tri- (or more) functional chain extender, such as tri-isocyanate. Branched copolymers may show improved creep characteristics.

Cross-linked copolymers are generally not preferred, since these copolymers are not easy to process.

Pre-Polymer Length and Ratio of Pre-Polymers A and B in Segmented Co-Polyesters.

In case of a crystallisable hard segment, the length (number average molecular weight, Mn) of the pre-polymer must be large enough to be able to crystallise in the copolymer. E.g. poly-ε-caprolactone (PCL) hard segment forming pre-polymer is preferably larger than 1000, more preferably larger than 2000, most preferably larger than 3000. A larger PCL pre-polymer length results in a phase separated morphology at a lower hard segment content, as will be shown in the results. The pre-polymer ratio at which phase separation is observed is therefore dependent on the pre-polymer lengths. In general, the lengths of the pre-polymers that form the soft and hard segment within a copolymer must have a value at which a phase separated morphology is observed, the extent of phase separation (compatibility) being favorable for the desired properties of the biomedical device.

The length of the soft segment forming pre-polymer (A) has an Mn of larger than 500, preferably larger than 1000, more preferably larger than 2000. The length of the prepolymers must be chosen in such a way that they are as large as is necessary to obtain a good phase separated morphology and good mechanical and thermal properties of the resulting copolymer. The pre-polymer length must be low enough to be miscible with the chain-extender at the polymerisation temperature, typically this means that Mn is lower than 10000. This is also the case in pre-polymers with structures aba and bab. The length of the outer segment is therefore dependent on the type of monomers used for both inner and outer segments.

Generally, a hard segment content in the range of 10-90 wt.%, preferably of 25-60%, results in flexible, thermoplastic materials with good mechanical properties at the temperature of application (viz. about 37° C. for medical applications).

Polymer Properties and Applications

Very high molecular weights of the multiblock copolymers are not necessary to obtain good mechanical properties. With an intrinsic viscosity of the copolymer of about 0.8 dl/g the initial mechanical properties will be sufficient for the production of medical devices. For drug delivery applications, the intrinsic viscosity may even be lower, preferably between 0.1-2 dl/g. High intrinsic viscosities are undesirable, because the polymer will be difficult to process. Typically, the intrinsic viscosity is larger than 0.1 dl/g and less than 10 dl/g. Preferably, the intrinsic viscosities lie between 1-4 dl/g for medical implants.

The multiblock segmented copolymers can be formed into surgical articles using any known technique such as, for example, extrusion, molding, solvent casting and freeze drying. The latter technique is used to form porous materials. Porosity can be tuned by addition of co-solvents, non-solvents and/or leachables. Copolymers can be processed (either solid or porous) as films, sheets, tubes, membranes, meshes, fibers, plugs, coatings, microspheres and other articles. Products can be either solid, hollow or (micro)porous. A wide range of surgical articles can be manufactured for applications in for example wound care, skin recovery, nerve regeneration, vascular prostheses, drug delivery, meniscus reconstruction, tissue engineering, coating of surgical devices, ligament and tendon regeneration, dental and orthopedic repair. The copolymers can be used alone or can be blended and/or co-extruded with other absorbable or non-absorbable polymers.

Furthermore, they can be used in pharmaceutical applications, e.g. for drug delivery, e.g. in the form of microspheres or membranes.

As will be illustrated in the examples below, the materials of the present invention have improved properties, including thermal, mechanical, processing compared to copolymers described in the prior art.

BRIEF DESCRIPTION OF THE DRAWINGS

FIG. 1 shows the heat flow endotherms of phase separated copolymers, being characterised by a Tg and a Tm of a copolymer.

FIG. 2 shows the relation between the glass transition temperature (Tg1 of first DSC run, Tg2 of second DSC run) and the $\epsilon$-caprolactone content of co-polyesters with different PCL pre-polymer lengths and of random copolymers of DL-Lactide and $\epsilon$-caprolactone: ♦ (closed diamonds): Tg1 of co-polyester with PCL2000 pre-polymer; ◇ (open diamond): Tg2 of co-polyester with PCL2000 pre-polymer; ■ (closed square): Tg1 of co-polyester with PCL3000 pre-polymer; △ (open square): Tg2 of co-polyester with PCL3000 pre-polymer; ● (closed circle): Tg1 of co-polyester with PCL4000 pre-polymer; ○(open circle): Tg2 of co-polyester with PCL4000 pre-polymer; ▲ (closed triangle): Tg1 of random co-polyester; A (open triangle): Tg2 of random co-polyester; *: Tg2 of co-polyester with lactide-$\epsilon$-caprolactone pre-polymer with Mn-2000.

FIG. 3 shows the relation between the melting temperature (peak maximum, Tm) of the first DSC run and the $\epsilon$-caprolactone content of co-polyesters with different PCL pre-polymer lengths and of random copolymers of DL-Lactide and $\epsilon$-caprolactone: ♦ (closed diamonds): Tm1 of co-polyester with PCL2000 pre-polymer; ■ (closed square): Tm1 of co-polyester with PCL3000 pre-polymer; ♦ (closed triangle): Tm1 of random co-polyester; ● (closed circle): Tm1 of co-polyester with PCL4000 pre-polymer.

FIG. 4 shows the relation between the melting enthalpy ($\Delta H$) of the first DSC run and the $\epsilon$F-caprolactone content of co-polyesters with different PCL pre-polymer lengths and of random copolymers of DL-Lactide and $\epsilon$-caprolactone: ♦ (closed diamonds): $\Delta H1$ of co-polyester with PCL2000 pre-polymer; ■ (closed square): $\Delta H1$ of co-polyester with PCL3000 pre-polymer; ♦ (closed triangle): $\Delta H1$ of random co-polyester; ● (closed circle): $\Delta H1$ of co-polyester with PCL4000 pre-polymer.

FIG. 5 shows the relation between the melting enthalpy ($\Delta H$) of the first DSC run and the average caprolactone sequence length, $\overline{L}_{Cap}$, of co-polyesters with different PCL pre-polymer lengths and of random copolymers of DL-Lactide and $\epsilon$-caprolactone: ♦ (closed diamonds): $\Delta H1$ of co-polyester with PCL2000 pre-polymer; ■ (closed square): $\Delta H1$ of co-polyester with PCL3000 pre-polymer; ▲ (closed triangle): $\Delta H1$ of random co-polyester; ● (closed circle): $\Delta H1$ of co-polyester with PCL4000 pre-polymer; *: $\Delta H1$ of co-polyester with lactide-$\epsilon$-caprolactone pre-polymer with Mn=2000.

FIG. 6 shows the relation between the average caprolactone sequence length, $\overline{L}_{Cap}$ and $\epsilon$-caprolactone content of co-polyesters with different PCL pre-polymer lengths and of random copolymers of DL-Lactide and $\epsilon$-caprolactone: ♦ (closed diamonds): $\overline{L}_{Cap}$ of co-polyester with PCL2000 pre-polymer; ■ (closed square): $\overline{L}_{Cap}$ of co-polyester with PCL3000 pre-polymer; ● (closed circle): $\overline{L}_{Cap}$ of co-polyester with PCL4000 pre-polymer; ▲ (closed triangle): $\overline{L}_{Cap}$ of random co-polyester. (closed circle): *: $\overline{L}_{Cap}$ of co-polyester with lactide-$\epsilon$-caprolactone pre-polymer with Mn=2000.

FIG. 7 shows the stress-strain behavior of the segmented co-polyesters with the PCL3000 pre-polymer with different PCL3000 content.

FIG. 8 shows the relation between the elastic modulus (E) and the $\epsilon$-caprolactone content of co-polyesters with different PCL pre-polymer lengths and of random copolymers of DL-Lactide and $\epsilon$-caprolactone: ♦ (closed diamonds): E of co-polyester with PCL2000 pre-polymer; ■ (closed square): E of co-polyester with PCL3000 pre-polymer; ♦ (closed triangle): E of random co-polyester.

EXAMPLES

Analysis Methods:

The following analysis methods were used in all examples, unless indicated otherwise.

The intrinsic viscosity was measured in chloroform at 25° C. using an Ubbelohde viscometer (according to ISO standard 1628-1).

Molecular weights were determined by Gel Permeation Chromatography at 30° C. using a Spectra Physics instrument equipped with 2 PL-Mixed-C columns (Polymer Labs), operating with tetrahydrofuran as eluent and with a Shodex RI-71 refractometer. Samples were dissolved in THF (1 mg ml$^{-1}$), the injection volume was 100 µl and the flow rate 1 ml min$^{-1}$ Calibration curves were obtained by polystyrene standards.

Pre-polymer and copolymer composition, monomer distribution (average sequence length, $\overline{L}_{Lac}$ and $\overline{L}_{Cap}$) were determined using $^1$H-NMR at 300 MHz in solutions in deuterated chloroform.

Thermal properties were determined under a nitrogen atmosphere using a Perkin-Elmer DSC-7, 5-10 mg samples being heated at a rate of 10° C. per minute, cooled down at a rate of 10° C. per minute, hold for 1 minute at −90° C. and heated again at a rate of 10° C. per minute. Tg and Tm were determined from the resulting DSC curves.

The stress strain behavior was determined on an Instron 4301 tensile tester. Thin films (0.25 mm) were measured at room temperature at a cross-head speed of 10 mm/minute. The ultimate tensile strength, the stress at 250% strain, the elongation at break and the initial modulus were determined from these measurements.

Films were prepared by evaporating a solution of the co-polyester in chloroform in a petri-dish during 7 days at room temperature.

Polymer properties are given in Tables 1-5.

The following notation is used to indicate the composition of the copolymers: e.g. the columns cap2000 and dl-lac/cap2000 in Table 1 give the ratio of the two pre-polymers (% w/w) (cap2000 is PCL pre-polymer with Mn=2000; dl-lac/cap2000 is DL-Lactide-ε-caprolactone pre-polymer with Mn=2000). The first column gives the molar co-monomer composition of the resulting copolymer: e.g. P(CL-DLLA) 80-20 contains 80 mol % ε-caprolactone (the total amount of ε-caprolactone in the two pre-polymers) and 20 mol % of dl-lactide.

Examples Prepolymers

Example 1

DL-Lactide-ε-caprolactone Prepolymer (Mn=2000)

32.82 grams (0.231 mol) DL-Lactide (Purac, the Netherlands) was introduced into a three-necked bottle under nitrogen atmosphere and was dried in vacuum at 45° C. for at least 8 hours. ε-Caprolactone (Acros, Belgium) is dried over $CaH_2$ and distilled under reduced pressure in a nitrogen atmosphere. 26.32 grams (0.231 mol) ε-caprolactone was added under a nitrogen flow. 2.68 grams (29.7 mmol) of 1,4-butanediol (Acros, distilled from 4 Ø molecular sieves after drying for 8 hours) was added. 24.8 mg stannous octoate (Sigma Corp) was added (M/I=8000). The mixture was magnetically stirred and reacted at 130° C. during 162 hours. $^1$H-NMR showed complete monomer conversion. The lactide:ε-caprolactone ratio in the pre-polymer was 48.4:51.6 (calculated by $^1$H-NMR). The calculated molecular weight (Mn) was 2080 and was confirmed by end-group analysis with $^1$H-NMR.

Example 2

ε-Caprolactone Prepolymer (Mn=2000)

193.98 grams (1.70 mol) ε-Caprolactone (see example 1 for purification) was introduced into a three-necked bottle under nitrogen atmosphere. 8.74 grams (97.0 mmol) of 1,4-butanediol (see example 1 for purification) was added. 78.7 mg stannous octoate (Sigma Corp) was added (M/I=9130). The mixture was magnetically stirred and reacted at 130° C. during 160 hours. $^1$H-NMR showed complete monomer conversion. The calculated molecular weight (Mn) was 2090 and was confirmed by end-group analysis with $^1$H-NMR Example 3

ε-Caprolactone Prepolymer (Mn=3000)

A pre-polymer with Mn=3000 was prepared in the same way as described in example 2. The calculated molecular weight (Mn) was 3160 and was confirmed by end-group analysis with $^1$H-NMR Example 4

General Polymerisation Method of Segmented co-Polyesters with Randomly Distributed Segments: P(CL-DLLA)

The PCL pre-polymer (2000, 3000 or 4000) and dl-lactide-ε-caprolactone pre-polymer are pre-heated until 70° C. until they become more liquid. The appropriate amounts of both pre-polymers are weighted into a glass ampoule supplied with nitrogen inlet and a mechanical stirrer. 1 equivalent of 1,4-butanediisocyanate (Bayer, distilled at reduced pressure) is added. The contents of the ampoule are quickly heated to 65° C. and then stirred mechanically for 15 minutes. As the mixture becomes viscous, the temperature is increased to 80° C. Stirring is stopped when the mixture becomes too viscous (between ½-½ hour) and the heating is continued for a maximum of 24 hours.

De ampoule is cooled to room temperature and post-polymerisation continues for 48 hrs. Then, the contents are isolated by dissolving the polymer in chloroform. The solution is filtered and poured into a petri-dish. The solvent is evaporated and after that the polymer film is dried in a vacuum oven at 40° C.

The polymer is stored in a sealed package at room temperature for at least 1 week before characterization takes place (thermal and mechanical properties and intrinsic viscosity). Polymer composition (average sequence length, $\overline{L}_{Lac}$ and $\overline{L}_{Cap}$) is determined by $^1$H-NMR.

Example 5

Synthesis of Random Co-Polyesters

Random copolymers were synthesized by a ring opening polymerization in the bulk initiated by stannous octoate. DL-Lactide (Purac, the Netherlands) and ε-Caprolactone (Acros, Belgium; dried over $CaH_2$ and distilled under reduced pressure in a nitrogen atmosphere) were charged into a clean, dry glass ampoule with nitrogen inlet. Stannous octoate was added (see Table 3) and the ampoule was placed in an oil bath at 120° C. The contents were kept under nitrogen atmosphere. The ampoules were heated for 5 days and were then cooled to room temperature. A sample of the polymer was taken for NMR measurements. The polymers were dissolved in chloroform and precipitated in ethanol (96%). Films for thermal and mechanical analysis were made from the purified copolymers. Intrinsic viscosities were measured from the purified copolymers.

Example 6

Preparation of Nerve Guides

Copolymers prepared according to the method in Example 4 with various ε-caprolactone/lactide ratios and with both PCL2000 and PCL3000 pre-polymers have been used for preparation of nerve guides. To this end, for each copolymer a polymer solution in chloroform was dip-coated on mandrels with various diameters. After dipping, the mandrel was placed horizontally and the solvent was allowed to evaporate during 5 minutes while rotating. This procedure was repeated until the desired wall thickness was obtained. The mandrel with the copolymer layer was placed first in ethanol and after that in distilled water. The tubes were removed from the mandrel and were cut into the appropriate lengths. They were placed in ethanol, followed by vacuum drying at 40° C. in order to remove monomer- and low molecular weight residues and organic solvents.

Example 7

Preparation of Microspheres

A copolymer (1 gram) prepared according to the method in Example 4 containing 39.3% (w/w) of PCL3000 prepolymer is dissolved in 50 ml of dichloromethane. A 3% polyvinylalcohol (PVA Mw=22.000) solution in 800 ml water is made. The solutions are filtered. The PVA solution is stirred at a rate of 200-800 rpm during the whole process. The polymer solution is added to the PVA solution. The solutions are stirred during 1.5 hours while evaporating the dichloromethane at reduced pressure. The stirring is stopped and the microspheres are collected from the aqueous phase, after which they are washed several times with water. Finally, the microspheres are dried by vacuüm or freeze-drying. According to this method, hollow microspheres with solid outer layer ($d_{50}$~25 μm) can be obtained. By slight modification of the process, also solid and porous particles and particles with a smaller or larger size can be prepared.

TABLE 1

Properties of segmented co-polyesters with PCL 2000 pre-polymer

| P(CL-DLLA) (mol %) | Composition (% w/w) | | [η] | $\bar{L}_{Cap}$ | $\bar{L}_{Lac}$ | $Tg_1$ (° C.) | $Tg_2$ (° C.) | $Tm_1$ (° C.) | $Tm_2$ (° C.) | $\Delta H_1$ (J/g) | $\Delta H_2$ (J/g) |
|---|---|---|---|---|---|---|---|---|---|---|---|
| | Cap2000 | dl-lac/cap 2000 | | | | | | | | | |
| 63.6-36.4 | 23.4 | 76.6 | 3.62 | 3.8 | 4.3 | −23.6 | −25.2 | 37.0 | — | 7.6 | — |
| 72.0-28.0 | 41.0 | 59.0 | 2.25 | 5.5 | 4.3 | −24.4 | −34.5 | 48.4 | — | 25.0 | — |
| 74.6-25.4 | 46.6 | 53.4 | 1.19 | 6.1 | 4.2 | −23.7 | −36.6 | 53.3 | 41.7 | 34.3 | 1.9 |
| 79.5-20.5 | 56.8 | 43.2 | 1.30 | 8.3 | 4.3 | −29.5 | −41.7 | 54.4 | 38.7 | 39.5 | 20.7 |

TABLE 2

Properties of segmented co-polyesters with PCL 3000 pre-polymer

| P(CL-DLLA) (mol %) | composition (% w/w) | | [η] | $\bar{L}_{Cap}$ | $\bar{L}_{Lac}$ | $Tg_1$ (° C.) | $Tg_2$ (° C.) | $Tm_1$ (° C.) | $Tm_2$ (° C.) | $\Delta H_1$ (J/g) | $\Delta H_2$ (J/g) |
|---|---|---|---|---|---|---|---|---|---|---|---|
| | Cap2000 | dl-lac/cap 2000 | | | | | | | | | |
| 67.7-32.3 | 33.3 | 66.7 | 1.99 | 4.0 | 3.8 | −16.8 | −29.6 | 49.0 | — | 26.7 | — |
| 70.6-29.4 | 39.3 | 60.7 | 1.27 | 4.8 | 4.0 | −17.1 | −34.3 | 57.7 | 45.4 | 32.0 | 1.82 |
| 75.3-24.7 | 48.9 | 51.1 | 1.31 | 6.2 | 4.1 | −20.7 | −40.0 | 58.4 | 45.7 | 39.2 | 18.7 |
| 76.5-23.5 | 51.4 | 48.6 | 1.13 | 6.4 | 3.9 | −22.1 | −38.9 | 57.4 | 45.7 | 42.1 | 21.3 |
| 79.2-20.8 | 57.0 | 43.0 | 1.61– | 7.6 | 4.0 | −24.1 | −42.6 | 53.7 | 45.0 | 44.3 | 26.2 |
| 51.7-48.3 | — | 100 | — | 2.4 | 4.1 | −13.9 | −11.3 | — | — | — | — |
| 100-0 *) | — | — | — | — | — | −58.1 | −61.0 | 64.0 | 59.0 | 81.7 | 63.0 |

*) (Mn = 80000)

TABLE 3

Properties of segmented co-polyesters with PCL 4000 pre-polymer

| P(CL-DLLA) (mol %) | composition (% w/w) | | [η] | $\bar{L}_{Cap}$ | $\bar{L}_{Lac}$ | $Tg_1$ (° C.) | $Tg_2$ (° C.) | $Tm_1$ (° C.) | $Tm_2$ (° C.) | $\Delta H_1$ (J/g) | $\Delta H_2$ (J/g) |
|---|---|---|---|---|---|---|---|---|---|---|---|
| | Cap4000 | dl-lac/cap 2000 | | | | | | | | | |
| 62.2-37.8 | 18.9 | 83.1 | 2.35 | 3.3 | 4.0 | −20.8 | −23.9 | 38.7 | — | 8.8 | — |
| 67.4-32.6 | 28.4 | 71.6 | 1.00 | 4.1 | 4.0 | −17.7 | −31.1 | 56.9 | 46.2 | 25.1 | 4.2 |

TABLE 4

Properties of random co-polyesters

| P(CL-DLLA) (mol %) | M/I | [η] | $\bar{L}_{Cap}$ | $\bar{L}_{Lac}$ | $Tg_1$ (° C.) | $Tg_2$ (° C.) | $Tm_1$ (° C.) | $Tm_2$ (° C.) | $\Delta H_1$ (J/g) | $\Delta H_2$ (J/g) |
|---|---|---|---|---|---|---|---|---|---|---|
| 74.5-25.5 | 7200 | 3.12 | 4.0 | 2.9 | −39.3 | −38.9 | 42.4 | — | 9.0 | — |
| 77.5-22.5 | 8500 | 3.78 | 7.1 | 4.1 | −37.4 | −46.9 | 43.7 | 39.7 | 28.5 | 7.1 |
| 80.2-19.8 | 4650 | 2.18 | 5.2 | 2.6 | −37.3 | −42.7 | 42.0 | — | 20.2 | — |

TABLE 5

Molecular weights of phase separated, segmented co-polyesters measured by GPC

| P(CL-DLLA) (mol %) | PCL length | [η] | Mw (·10⁻³) | MN (·10⁻³) | D |
|---|---|---|---|---|---|
| 63.6-36.4 | 2000 | 3.62 | 234.0 | 117.3 | 2.0 |
| 74.6-25.4 | 2000 | 2.08 | 287.0 | 89.0 | 3.23 |
| 67.7-32.3 | 3000 | 1.99 | 171.9 | 83.3 | 2.07 |
| 75.3-24.7 | 3000 | 1.31 | 287.9 | 115.9 | 2.50 |

Results and Discussion

Summary:

Segmented co-polyesters build of a DL-lactide-ε-caprolactone soft segment (with Mn 2000) and of a PCL hard segment (with Mn 3000 or Mn 4000) and with a hard segment content of 33-57% and 28% (w/w), respectively, are flexible, thermoplastic elastomers with good mechanical and thermal properties. This type of material seems very promising for being used for nerve guides capable of bridging nerve defects larger than 2 cm.

As a reference material, random copolymers of D,L-Lactide and ε-caprolactone with similar monomer compositions as the segmented copolymers have been prepared. The lower degree of phase separation and the lower melting point of the crystalline phase makes them less applicable as polymers for biomedical devices. These differences are caused by a different monomer distribution: in a block-copolymer such as the phase separated lactide/ε-caprolactone based co-polyester, the average sequence length of the monomers will be longer and the sequence length distribution will be much smaller than in a 'random' copolymer. The average monomer sequence length will affect the thermal- and mechanical properties of the copolymer.

Results:

Phase separated segmented co-polyesters with structure (ab)r consisting of a poly-ε-caprolactone hard phase and a poly(dl-lactide-ε-caprolactone) soft phase have been prepared with various ratio's of dl-lactide and ε-caprolactone. A non-random distribution of lactide and ε-caprolactone is obtained: the monomer sequence is determined by those of the individual building blocks. A small part of the poly(ε-caprolactone) prepolymer is amorphous and is present in the amorphous poly(lactide-ε-caprolactone) phase; the major part of the poly-ε-caprolactone is present as the crystalline hard phase. The degree of phase-mixing and the polymer properties are dependent on the pre-polymer chain length and -ratio.

Phase separation occurs above a certain threshold of the hard phase content. The content at which the hard phase is formed (crystallisation) is related to the molecular weight (chain length) of the pre-polymer(s). Segmented polyesters based on PCL (poly-ε-caprolactone) hard segments and lactide-ε-caprolactone soft segments and with Mn=2000 of the soft segment forming pre-polymer show a good phase separation with a pre-polymer content of 40-45% of the PCL hard segment forming phase with Mn=2000, 33% of a pre-polymer with Mn=3000, and 28% of a pre-polymer with Mn=4000, respectively. The longer PCL segment results in a better phase separation beginning at lower concentration. The effects of the composition of the segmented copolymers on the degree of phase separation are clarified by the thermal- and mechanical properties. FIGS. 2-6 show the differences in thermal properties and monomer distribution of segmented co-polyesters with soft segment pre-polymer length of 2000 and hard segment pre-polymer lengths of 2000 (cap2000) and 3000 (cap3000) and 4000 (cap4000), respectively. Also, the properties of the random poly(dl-lactide-ε-caprolactone) prepared at 120° C. during 5 days are shown. The glass transition temperature (Tg) of the soft segment in cap3000 and cap4000 is higher than that in cap2000 with a similar monomer ratio (FIG. 2): the amorphous phase of cap3000 and cap4000 contains less amorphous PCL than that of cap2000, due to a better phase separation. Both are higher than the values of Tg of the random copolymers with similar monomer composition. Furthermore, the higher the ε-caprolactone content within a copolymer range with the same PCL length, the lower the Tg will be, due to partly mixing of the amorphous PCL with the soft segment. In case of cap2000 and cap4000, the Tg of the copolymer with a low PCL content (23% and 19% w/w, respectively) is almost as low as the Tg measured in the second run, where the copolymer is completely amorphous. In general, in the second DSC run, the Tg decreases with ε-caprolactone content and is independent of the monomer distribution (segmented or random).

The melting points of the hard segment (Tm) are shown in FIG. 3. The melting point (maximum of melting peak) increases with ε-caprolactone content and is highest for the cap3000 series with a maximum value at a ε-caprolactone content of about 75%. A cap4000 copolymer with a caprolactone content of 67.4% has a much higher melting point than the cap3000 copolymer with a similar monomer composition. This is the result of a better phase separation of the longest PCL segment. The melting points with the highest ε-caprolactone content within the cap3000 series are somewhat lower than expected, probably caused by incomplete phase separation. The melting temperatures of the segmented copolymers with a large ε-caprolactone content are only a little lower than those of the PCL pre-polymer (58-60° C.) and of PCL with Mn=80000, having a Mp of 63° C. Melting points of the random copolymers are much lower (42-44° C.) than those of the segmented copolymers and are also much broader (the onset of the melting peak begins at 25-30° C.). This proves that there is a better phase separation in the segmented copolymers than in the random copolymers. In the second DSC run, melting temperatures of the segmented copolymers are lower (40-45° C.) due to incomplete phase separation. Re-crystallization does not occur at the lowest δ-caprolactone contents: the cap4000 copolymers start to re-crystallize at a lower ε-caprolactone content than the cap3000 and cap2000 copolymers. Therefore, the annealing time must be long enough to obtain complete phase separation. Melting temperatures of the random copolymers are also much lower (38-40° C.) or they are absent in the second run. These results are comparable to those found in literature (Lemmouchi et. al., Hiljanen-Vainio et. al.)

FIG. 4 shows the melting enthalpy (ΔH) of the three segmented copolymers and the random copolymer versus the δ-caprolactone content. The melting enthalpies of the cap3000 and cap4000 copolymers are largest and increase, both with the same trend, almost linearly with increasing ε-caprolactone content. A larger ε-caprolactone content leads to a larger melting enthalpy and therefore to a larger degree of crystallinity (as a reference, the melting enthalpy of the PCL pre-polymers is about 100 J/g).

The melting enthalpy of the random copolymers is not linearly dependent on the e-caprolactone content. In fact, it is linearly related to the average monomer sequence length of ε-caprolactone, $\overline{L}_{Cap}$. FIG. 5 shows this relationship for the random- and segmented copolymers. Clearly, the cap3000 and cap4000 copolymers show larger melting enthalpies than the cap2000 and the random copolymers, at a similar average ε-caprolactone sequence length. In FIG. 6 it is shown that within the cap2000, cap3000 and cap4000 series, $\overline{L}_{Cap}$ increases with ε-caprolactone content, the relation being independent of the PCL length. However, this is not the case for the random copolymers. The monomer distribution is determined by the polymerisation conditions. The random copolymers are all prepared at the same polymerisation time and temperature, but with a different catalyst concentrations. A lower catalyst concentration results in longer monomer sequence lengths and therefore, more crystallization occurs. The segmented copolymers are prepared by mixing of two pre-polymers: the average ε-caprolactone sequence length can be increased by adding more of the PCL pre-polymer. By this method, the average sequence length of lactide does not change and will be constant within a copolymer series (not shown). This means that during the short time of chain-extending, no trans-esterification reaction occurs and the final polymer properties are only dependent on the pre-polymer properties.

Concerning the thermal properties, the segmented copolymers are more suitable for biomedical applications than the random copolymers. Depending on the type of application, the monomer ratio can be changed while keeping the same thermal (and mechanical) properties simply by changing the length of the pre-polymers.

Mechanical Properties

Mechanical properties of the segmented copolymers are dependent on the degree of phase separation and therefore on the degree of crystallinity. As an example, the stress strain behavior of the segmented co-polyesters with the PCL pre-polymer with Mn=3000 is shown in FIG. 7. The stress at a certain degree of elongation (e.g 400%) increases with PCL content, so is the modulus. The tensile strength is also dependent on the amount of strain induced crystallization, which occurs when amorphous PCL starts to crystallize as a result of orientation. FIG. 8 presents the relation between the initial modulus and the ε-caprolactone content: the modulus of the PCL3000 containing copolymer is higher than that of the PCL2000 containing copolymer with the same s-caprolactone content, as a result of the higher degree of crystallinity (melting enthalpy) of the former. The modulus of the random copolymers is variable with the ε-caprolactone content and can be as high as those of the segmented copolymers. In fact, the modulus is related to the average monomer sequence length, $\overline{L}_{Cap}$, a property that can be altered by varying the polymerisation conditions. In general, the modulus is related to the average monomer sequence length, $\overline{L}_{Cap}$, in the same way as is the melting enthalpy as has been shown in FIG. 5. Although, from a mechanical point of view, the random copolymers can be as good as the segmented copolymers, the thermal properties are inferior to those of the segmented copolymers.

The modulus of the segmented co-polyesters can be much higher than those of amorphous, lactide rich copolymers (e.g. poly(dl-lactide-ε-caprolactone) with a 50:50 monomer ratio has an elastic modulus of 1-2 MPa). Therefore, segmented copolymers, even with a rather low ε-caprolactone content, can be processed into materials with a high modulus. For an application such as an artificial nerve guide for bridging long nerve gaps, a modulus that is high enough to prevent compression of the nerve guide is required. This can be accomplished by using segmented co-polyesters.

REFERENCES

1. European patent application nr. 02075481.8: DL-Lactide-ε-caprolactone copolymers.
2. C. G. Pitt, M. M. Gratzl, G. L. Kimmel, J. Surles and A. Schindler, The degradation of poly(D,L-lactide), poly(ε-caprolactone) and their copolymers in vitro. *Biomaterials* 2 (1981) 215-220.
3. M. Malin, M. Hiljainen-Vainio, T. Karjalainen, J. Seppala, Biodegradable lactone copolymers II. Hydrolytic study of ε-caprolactone and lactide copolymers. *J. Appl. Polym. Sci.* 59 (1996) 1289-1298.
4. M. Hiljainen-Vainio, T. Karjalainen, J. Seppala, Biodegradable lactone copolymers. I. Characterisation and mechanical behaviour of ε-caprolactone and lactide copolymers. *J. Appl. Polym. Sci.* 59 (1996) 1281-1288.
5. Y. Lemmouchi, E. Schact, P. Kageruka, R. De Deken, B. Diarra, O. Diall and S. Geerts, Biodegradable polyesters for controlled release of trypanocidal drugs: in vitro and in vivo studies. *Biomaterials* 19 (1998) 1827-1837.

The invention claimed is:

1. Biodegradable, linear, phase separated multiblock copolymer, comprising:
    segments of a linear soft biodegradable prepolymer (A) having a glass transition temperature ($T_g$) lower than 37° C.; and
    segments of a linear hard biodegradable prepolymer (B) having a melting point temperature ($T_m$) of 40-100° C., the segments being linked by a multifunctional chain-extender, wherein said chain-extender is a difunctional, aliphatic molecule,
    wherein the segments of the soft biodegradable prepolymer (A) and the segments of the hard biodegradable prepolymer (B) are randomly distributed in the copolymer.

2. Copolymer according to claim 1, wherein prepolymer (A) comprises ester and/or carbonate groups.

3. Copolymer according to claim 1, wherein a polyether is present as an additional prepolymer.

4. Copolymer according to claim 1, wherein pre-polymer (A) comprises reaction products of ester forming monomers selected from diols, dicarboxylic acids and hydroxycarboxylic acids.

5. Copolymer according to claim 1, wherein prepolymer (A) comprises reaction products of cyclic monomers and/or non-cyclic monomers.

6. Copolymer according to claim 5, wherein said cyclic monomers are selected from glycolide, lactide (L, D or L/D), ε-caprolactone, δ-valerolactone, trimethylene carbonate, tetramethylenecarbonate, 1,5-dioxepane-2-one, 1,4-dioxane-2-one (para-dioxanone) and/or cyclic anhydrides such as oxepane-2,7-dione.

7. Copolymer according to claim 5, wherein said non-cyclic monomers are selected from succinic acid, glutaric acid, adipic acid, sebacic acid, lactic acid, glycolic acid, hydroxybutyric acid, ethylene glycol, diethyleneglycol, 1,4-butanediol and/or 1,6-hexanediol.

8. Copolymer according to claim 3, wherein said polyether is selected from PEG (polyethylene glycol), PEG-PPG (polypropylene glycol), PTMG (polytetramethyleneether glycol) and combinations thereof.

9. Copolymer, according to claim 1, wherein prepolymer (A) is prepared by a ring-opening polymerisation initiated by a diol or di-acid compound.

10. Copolymer according to claim 8, wherein PEG is an initiator with a molecular weight of 150-4000.

11. Copolymer according to claim 1, wherein prepolymer (B) is prepared by a ring-opening polymerisation initiated by a diol or di-acid compound.

12. Copolymer according to claim 1, wherein prepolymer (B) contains a crystallisable amount of ε-caprolactone, δ-valerolactone, para-dioxanone, polyhydroxyalkanoate, aliphatic polyanhydride.

13. Copolymer according to claim 12, wherein pre-polymer (B) is poly-ε-caprolactone.

14. Copolymer according to claim 13, wherein pre-polymer (B) has an average molecular weight ($M_n$) of larger than 1000.

15. Copolymer according to claim 13 wherein the content of prepolymer (B) is 10-90 wt. %.

16. Copolymer according to claim 1, having an intrinsic viscosity of at least 0.1 dl/g.

17. An implant comprising a copolymer according to claim 1.

18. Copolymer according to claim 2, wherein the ester and/or carbonate groups are in combination with polyethers.

19. Copolymer according to claim 8, wherein PEG is an initiator with a molecular weight of 150-2000.

20. Copolymer according to claim 8, wherein PEG is an initiator with a molecular weight of 300-1000.

21. Copolymer according to claim 13, wherein pre-polymer (B) has and average molecular weight ($M_n$) of larger than 2000.

22. Copolymer according to claim 13, wherein pre-polymer (B) has and average molecular weight ($M_n$) of larger than 3000.

23. Copolymer according to claim 13 wherein the content of prepolymer (B) is 30-50 wt. %.

24. Copolymer according to claim 1, having an intrinsic viscosity of between 1-4 dl/g.

* * * * *

UNITED STATES PATENT AND TRADEMARK OFFICE
CERTIFICATE OF CORRECTION

PATENT NO.        : 8,674,033 B2
APPLICATION NO.   : 10/521126
DATED             : March 18, 2014
INVENTOR(S)       : Hissink et al.

It is certified that error appears in the above-identified patent and that said Letters Patent is hereby corrected as shown below:

IN THE SPECIFICATION:

Column 5, line 47:
Now reads: "s-caprolactone"
Should read: -- ε-caprolactone --

Column 5, line 48:
Now reads: "AH"
Should read: -- ΔH --

Column 9, line 65:
Now reads: "(3)"
Should read: -- (B) --

Column 11, line 54:
Now reads: "Δ (open square)"
Should read: -- □ (open square) --

Column 11, line 58:
Now reads: "A (open triangle)"
Should read: -- Δ (open triangle) --

Column 11, line 67:
Now reads: "♦ (closed triangle)"
Should read: -- ▲ (closed triangle) --

Column 12, line 9:
Now reads: "♦ (closed triangle)"
Should read: -- ▲ (closed triangle) --

Signed and Sealed this
Fifteenth Day of July, 2014

Michelle K. Lee
*Deputy Director of the United States Patent and Trademark Office*

CERTIFICATE OF CORRECTION (continued)
U.S. Pat. No. 8,674,033 B2

IN THE SPECIFICATION: (Continued)

Column 12, line 42:
Now reads: "♦ (closed triangle)"
Should read: -- ▲ (closed triangle) --

Column 12, line 4:
Now reads: "ϵF-caprolactone"
Should read: -- ε-caprolactone --

Column 14, line 17:
Now reads: "(between ½-½ hour)"
Should read: -- (between ½-1½ hour) --

Column 19, line 39:
Now reads: "s-caprolactone"
Should read: -- ε-caprolactone --

UNITED STATES PATENT AND TRADEMARK OFFICE
CERTIFICATE OF CORRECTION

PATENT NO. : 8,674,033 B2
APPLICATION NO. : 10/521126
DATED : March 18, 2014
INVENTOR(S) : Hissink et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2093 days.

Signed and Sealed this
Twenty-ninth Day of September, 2015

Michelle K. Lee
*Director of the United States Patent and Trademark Office*